(12) United States Patent
Bani-Hashemi et al.

(10) Patent No.: US 7,912,176 B2
(45) Date of Patent: Mar. 22, 2011

(54) DOSE-SPARING TOMOGRAPHIC IMAGING

(75) Inventors: Ali Bani-Hashemi, Walnut Creek, CA (US); Christopher Amies, Pleasant Hill, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 129 days.

(21) Appl. No.: 12/210,983

(22) Filed: Sep. 15, 2008

(65) Prior Publication Data

US 2010/0067647 A1 Mar. 18, 2010

(51) Int. Cl.
*A61B 6/03* (2006.01)
(52) U.S. Cl. ........................................................ 378/16
(58) Field of Classification Search ................ 378/4, 16, 378/9, 10
See application file for complete search history.

(56) References Cited

U.S. PATENT DOCUMENTS

| | | | | |
|---|---|---|---|---|
| 4,998,268 | A | * | 3/1991 | Winter ............................ 378/63 |
| 5,379,333 | A | * | 1/1995 | Toth ................................ 378/16 |
| 6,393,090 | B1 | * | 5/2002 | Hsieh et al. ....................... 378/4 |
| 2007/0242797 | A1 | * | 10/2007 | Stewart et al. .................. 378/16 |

OTHER PUBLICATIONS

K. Sourbelle et al., "Reconstruction from truncated projections in CT using adaptive detruncation", Eur Radiol (2005) 15: pp. 1008-1014, 7 pages total.
R. Cityala et al., "Artifact reduction in truncated CT using Sinogram completion", 8 pages total, (2005).
Anders H. Andersen, "Algebraic Reconstruction in CT from Limited View", IEEE Transactions on Medical Imaging, vol. 8, No. 1, Mar. 1989, pp. 50-55, 6 pages total.
Mark A. Anastasio et at., "A preliminary investigation of local tomography for megavoltage CT imaging", Medical Physics, vol. 30, No. 11, Nov. 2003, © 2003 Am. Assoc. Phys. Med., pp. 2969-2980, 12 pages total.

* cited by examiner

*Primary Examiner* — Chih-Cheng G Kao

(57) ABSTRACT

A system includes emission of a first plurality of radiation beams from respective ones of a first plurality of locations along a first arc, acquisition of a first plurality of projection images of a target based on the first plurality of radiation beams, emission of a second plurality of radiation beams from respective ones of a second plurality of locations along a second arc, acquisition of a second plurality of projection images of the target based on the second plurality of radiation beams, and generation of a three-dimensional image of the target based on the first plurality of projection images and the second plurality of projection images, wherein a density of the first plurality of locations along the first arc is less than the density of the second plurality of locations along the second arc.

15 Claims, 8 Drawing Sheets

DOSE-SPARING TOMOGRAPHIC IMAGING

BACKGROUND

1. Field

The embodiments described below relate generally to imaging, and more particularly to the generation of tomographic images.

2. Description

Three-dimensional imaging systems are commonly used to generate images of an internal portion of a body. In one example, a computed tomography (CT) system includes an X-ray source and a radiation receiver that are mounted to face one another on opposite sides of a ring. A body is positioned within the ring so that a portion of interest lies between the X-ray source and the radiation receiver. The X-ray source then emits X-ray radiation that passes through the portion of interest and is received by the radiation receiver.

The receiver produces a set of data that represents the attenuative properties of tissues that lie between the X-ray source and the receiver. This set of data comprises a projection image. The ring is then rotated in order to rotate the X-ray source and the radiation receiver around the portion of interest. During the rotation, the X-ray source transmits radiation toward the receiver and the receiver produces projection images corresponding to various rotational angle positions. A three-dimensional image of the portion of interest may be generated from the projection images using known reconstruction techniques.

The three-dimensional image may be used to diagnose illness, to plan radiation therapy, to confirm patient positioning prior to therapy, and/or to perform image-guided radiotherapy (IGRT). IGRT, for example, requires frequent (e.g., daily) imaging in order to reduce treatment margin and increase target dose accumulation.

Healthy tissue is exposed to radiation during imaging as described above. For example, treatment of breast tissue using IGRT exposes the non-cancerous breast to non-trivial amounts of radiation. It is feared that such radiation may result in future cancer of the non-cancerous breast.

Techniques are desired to provide adequate imaging of a volume of interest while reducing a dose absorbed by other patient volumes.

SUMMARY

To address at least the foregoing, some embodiments provide a system, method, apparatus, and means to emit a first plurality of radiation beams from respective ones of a first plurality of locations along a first arc, acquire a first plurality of projection images of a target based on the first plurality of radiation beams, emit a second plurality of radiation beams from respective ones of a second plurality of locations along a second arc, acquire a second plurality of projection images of the target based on the second plurality of radiation beams, and generate a three-dimensional image of the target based on the first plurality of projection images and the second plurality of projection images. A density of the first plurality of locations along the first arc may be less than the density of the second plurality of locations along the second arc.

In some aspects, at least one of the first plurality of radiation beams exhibits a first divergence angle, and at least one of the second plurality of radiation beams exhibits a second divergence angle different from the first divergence angle. Additionally or alternatively, the at least one of the first plurality of radiation beams is associated with a first intensity, and the at least one of the second plurality of radiation beams is associated with a second intensity different from the first intensity.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated by for carrying out the described embodiments. Various modifications, however, will remain readily apparent to those in the art.

Figure 1:
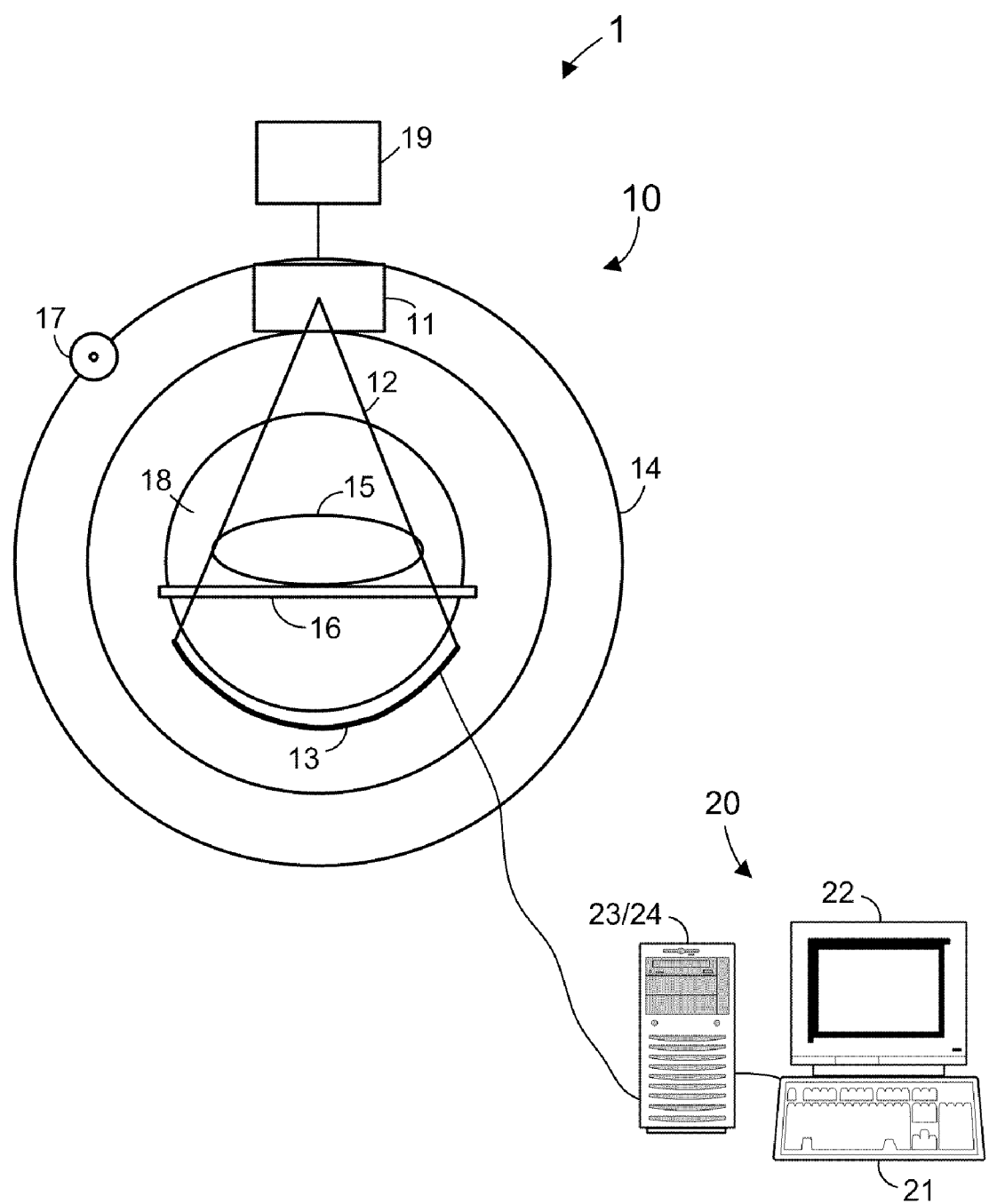
FIG. 1 is a diagram illustrating an image acquisition system according to some embodiments.

FIG. 1 illustrates CT system 1 according to some embodiments. CT system 1 comprises CT scanner 10 and operator console 20. In some embodiments, CT system 1 operates to emit a first plurality of radiation beams from respective ones of a first plurality of locations along a first arc, to acquire a first plurality of projection images of a target based on the first plurality of radiation beams, to emit a second plurality of radiation beams from respective ones of a second plurality of locations along a second arc, and to acquire a second plurality of projection images of the target based on the second plurality of radiation beams.

In some embodiments, CT system 1 may further operate to generate a three-dimensional image of the target based on the first plurality of projection images and the second plurality of projection images. A density of the first plurality of locations along the first arc may be less than the density of the second plurality of locations along the second arc.

CT scanner 10 is located in a CT room and includes X-ray source 11 for emitting fan-shaped beam 12 of X-ray radiation toward imaging device 13. X-ray source 11 may include known elements for controlling a shape of fan-shaped beam 12. Both X-ray source 11 and imaging device 13 are mounted on ring 14 such that they may be rotated through 360 degrees while maintaining the physical relationship therebetween.

In general operation, patient 15 is positioned on bed 16 to place a portion of patient 15 between X-ray source 11 and imaging device 13. Next, X-ray source 11 and imaging device 13 are rotated by rotation drive 17 around cavity 18 in which patient 15 lies. During this rotation, X-ray source 11 is powered by high-voltage generator 19 to emit X-ray radiation toward imaging device 13. Imaging device 13 receives the radiation and produces a projection image for each projection angle.

The projection images are transmitted to operator console 20. Operator console 20 calculates attenuation coefficients (e.g., Hounsfield numbers) of predetermined points based on the images. The attenuation coefficients may be used to generate a three-dimensional image representing the portion of patient 15 that lies between X-ray source 11 and imaging device 13.

Operator console 20 may be in a room other than a room in which CT scanner 10 is located, in order to protect its operator from radiation. Operator console 20 includes input device 21 for receiving instructions from an operator and output device 22. Output device 22 may comprise a monitor for presenting operational parameters of CT scanner 10, projection images acquired by imaging device 13, three-dimensional images generated based on the projection images, interfaces for receiving operator instructions, and/or operator alerts.

Input device 21 and output device 22 are coupled to processor 23 and storage 24. Processor 23 may execute program code to perform any of the acquisitions, determinations, iterations and generations described herein. The program code may be stored in storage 24, which may comprise one or more storage media of identical or different types, including but not limited to a fixed disk, a floppy disk, a CD-ROM, a DVD-ROM, a Zip™ disk, and a magnetic tape.

Storage 24 may also store program code to generate and/or modify an imaging plan according to some embodiments. Accordingly, storage 24 may also store imaging plans in accordance with any currently- or hereafter-known format. The imaging plans may comprise scripts that are automatically executable by elements of system 1 to acquire images according to some embodiments. For example, an imaging plan may specify various locations around ring 14 from which to emit radiation beams, and a beam divergence and beam intensity corresponding to each location.

A hardware environment according to some embodiments may include fewer or more elements than those shown in FIG. 1. In addition, embodiments are not limited to the devices and/or to the illustrated environment.

Figure 2:
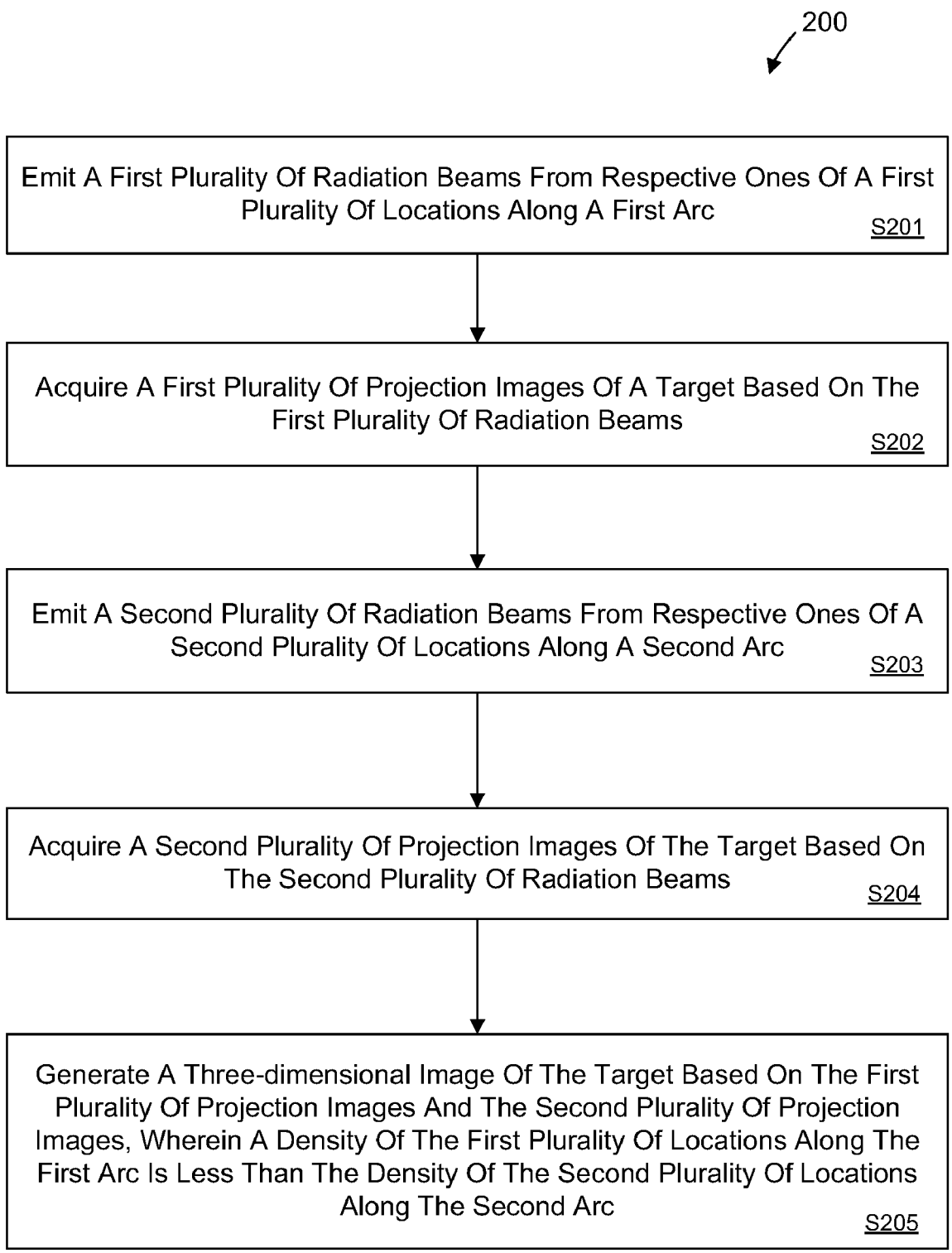
FIG. 2 comprises a flow diagram illustrating process steps according to some embodiments.

FIG. 2 is a flow diagram of process steps 200 executed by system 1 according to some embodiments. Process steps 200 may be embodied, in whole or in part, by hardware of and/or software executed by elements including but not limited to those of CT scanner 10 and computer system 20. Software embodying process steps 200 may be stored by any medium, including a fixed disk, a floppy disk, a CD-ROM, a DVD-ROM, a Zip™ disk, and a magnetic tape. Some or all of such software may also be stored in one or more devices.

Figure 3:
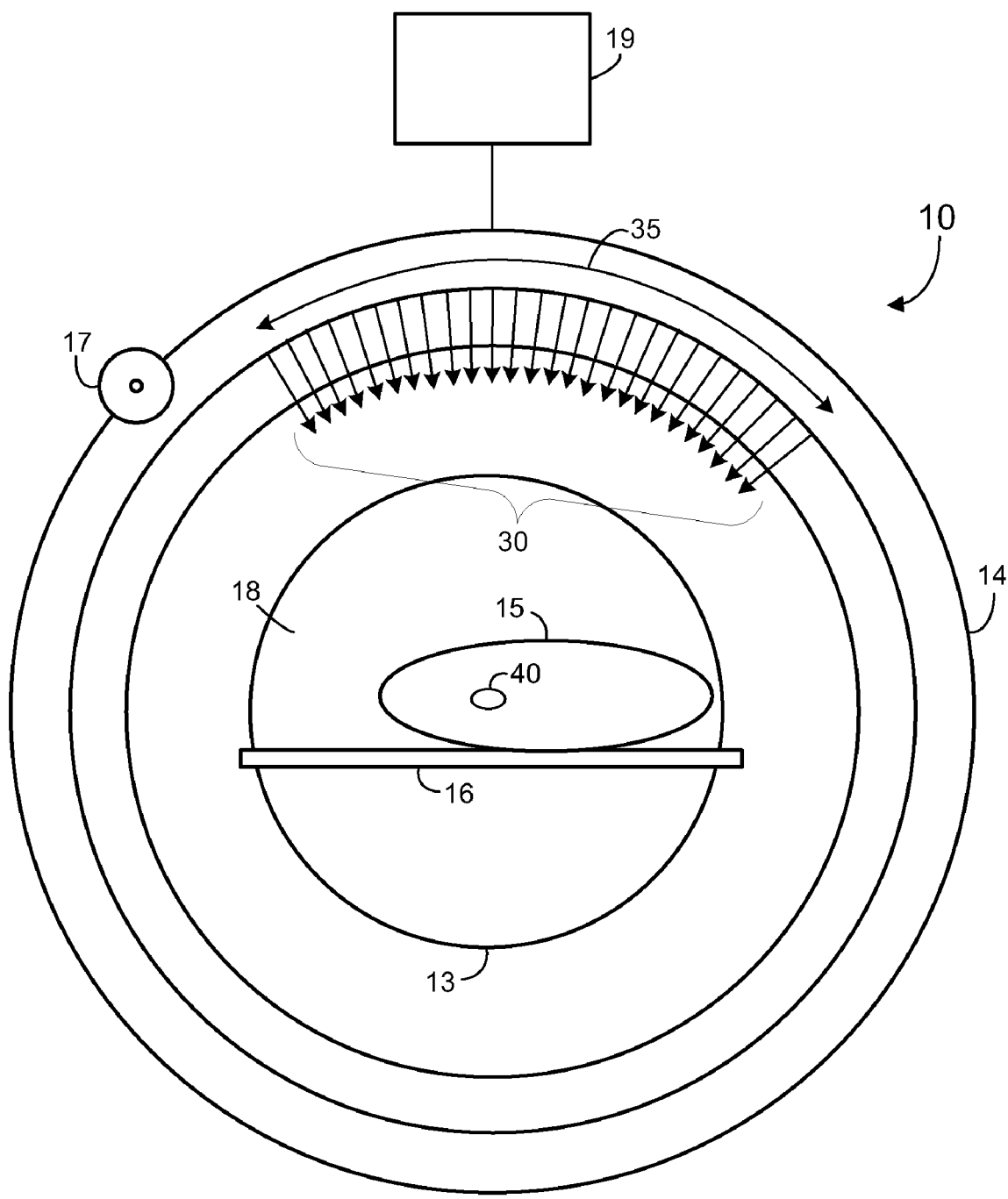
FIG. 3 is a diagram illustrating radiation emission locations according to some embodiments.

Initially, at step S201, a first plurality of radiation beams are emitted from respective ones of a first plurality of locations along a first arc. FIG. 3 is a view of CT scanner 10 to illustrate S201 according to some embodiments. Arrows 30 represent axes of radiation beams emitted from the depicted locations along arc 35.

FIG. 3 also shows target volume 40 of patient 15. Patient 15 is displaced from the position shown in FIG. 1 such that target 40 is located at a center of ring 14. In comparison to other techniques, such positioning may allow imaging of target 40 while reducing a dose received by other volumes of patient 15.

A first plurality of projection images of target 40 are acquired at S202 based on the emitted first plurality of radiation beams. In this regard, S201 and S202 may occur iteratively over a common period of time. For example, imaging device 16 (not shown) is moved substantially normal to an axis 30, a radiation beam having the axis 30 is emitted, and imaging device 16 acquires a projection image based on received radiation. This sequence may then repeat for each of the locations shown in FIG. 3.

Figure 4:
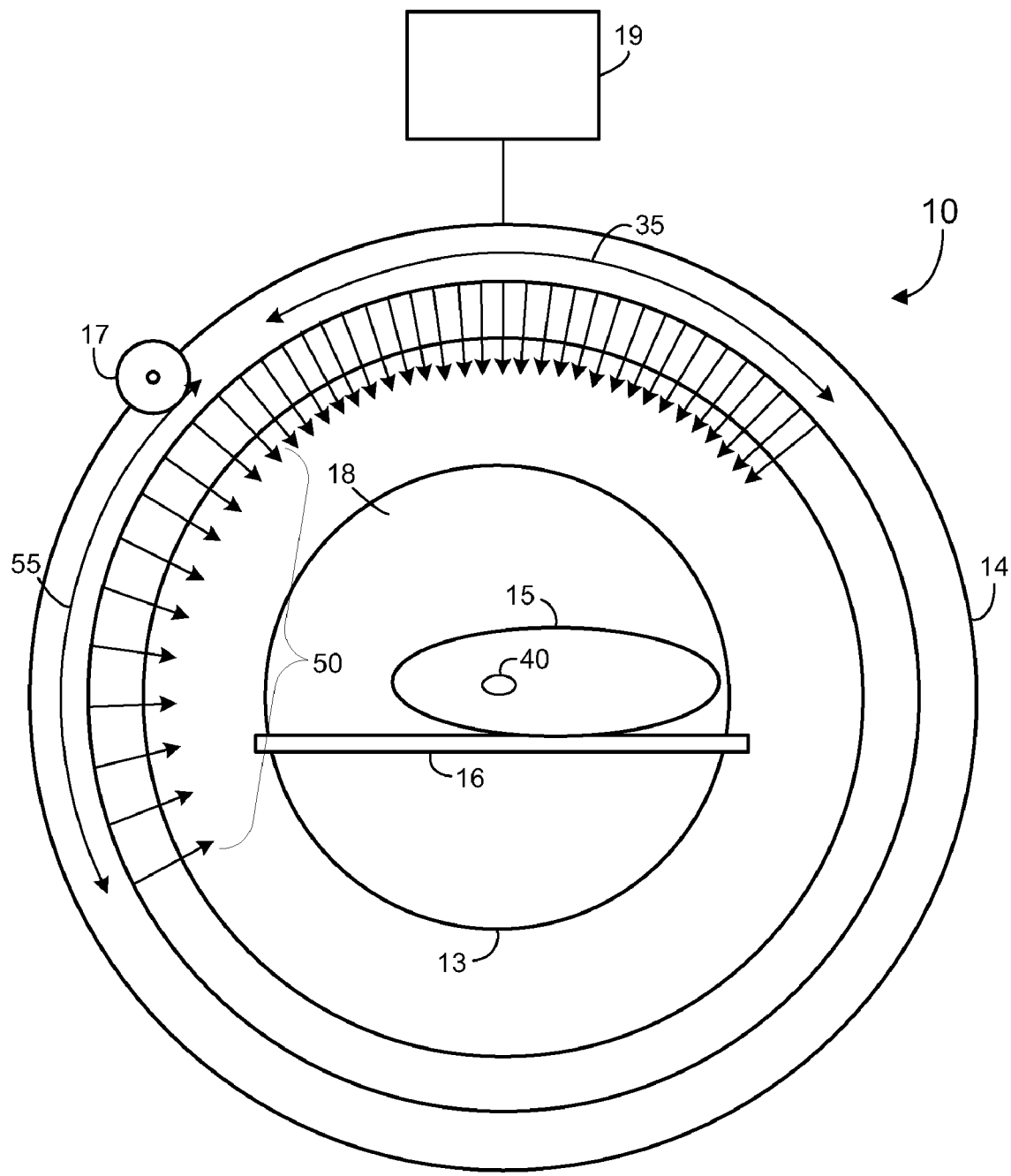
FIG. 4 is a diagram illustrating radiation emission locations according to some embodiments.

A second plurality of radiation beams are emitted at step S203 from respective ones of a second plurality of locations along a second arc. FIG. 4 is a view of CT scanner 10 to illustrate S203 according to some embodiments. Arrows 50 represent axes of radiation beams emitted from the depicted locations along arc 55. As described above, a second plurality of projection images of target 40 are then acquired at S204 based on the emitted second plurality of radiation beams.

As shown in FIG. 4, the density of the first plurality of locations along arc 35 is greater than the density of the second plurality of locations along arc 55. These locations and relative densities may be selected to allow satisfactory imaging of target 40 while reducing a dose received by other volumes of patient 15. In contrast, conventional systems acquire projection images by emitting radiation from evenly-spaced locations.

Figure 5:
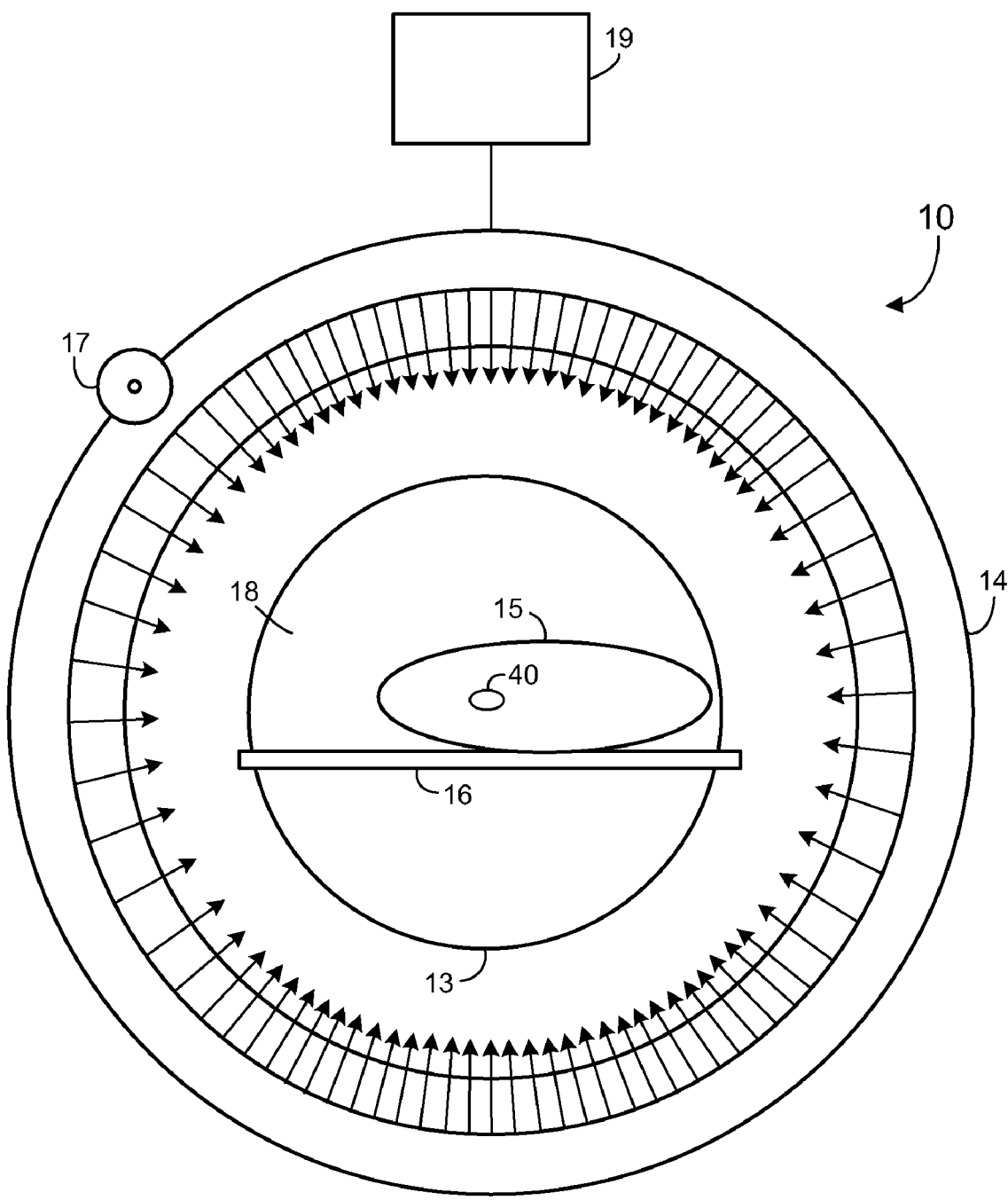
FIG. 5 is a diagram illustrating radiation emission locations according to some embodiments.

According to the present example, it will be assumed that additional projection images are acquired after S204 based on additional emitted radiation. FIG. 5 illustrates locations from which the additional radiation may be emitted. The locations vary in density as described above with respect to the first and second plurality of locations.

Figure 6:
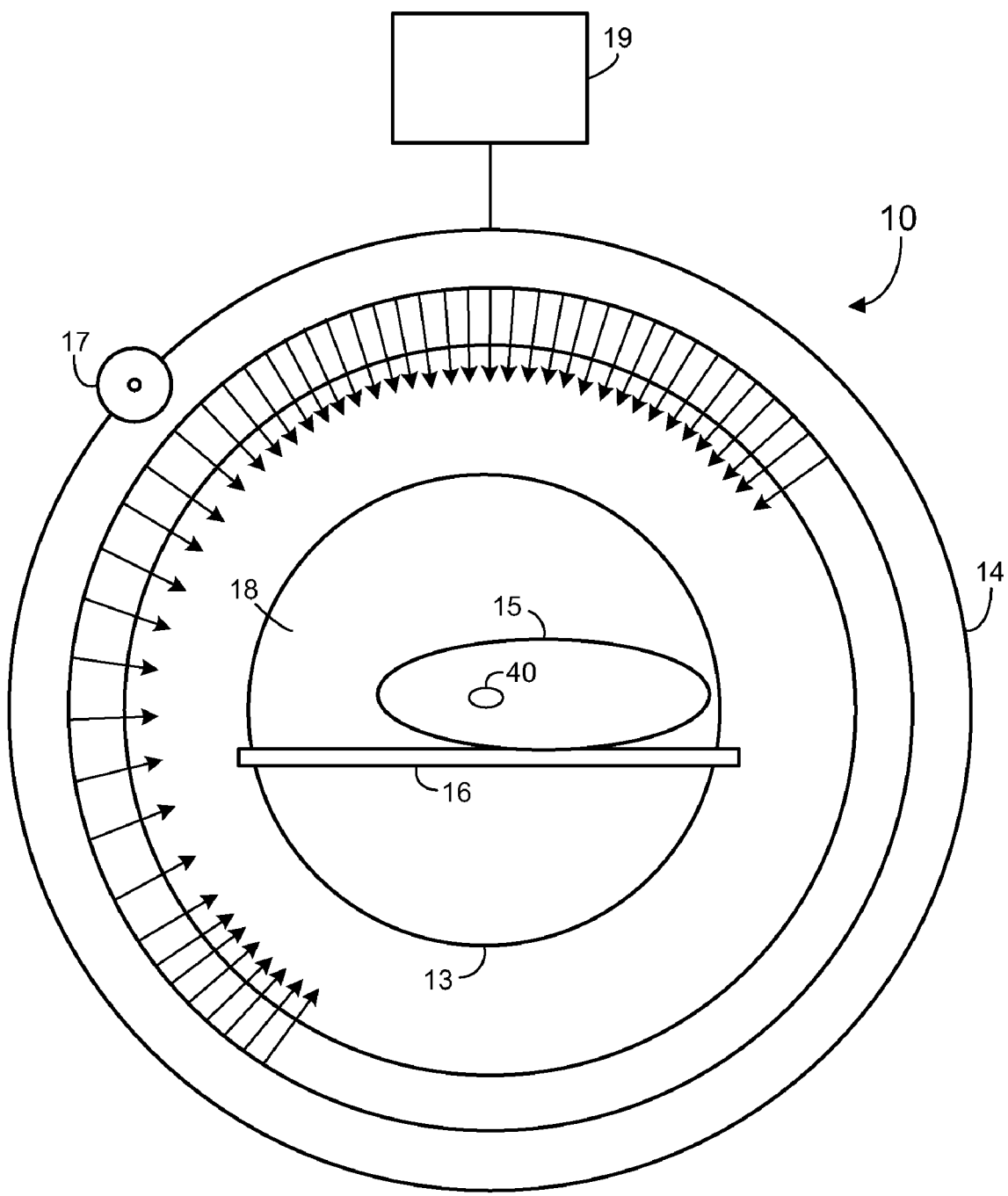
FIG. 6 is a diagram illustrating radiation emission locations according to some embodiments.

In some embodiments, the additional projections do not complete a 360 degree arc as shown in FIG. 5. For example, as shown in FIG. 6, the additional projections may be acquired to complete an arc around target 40 equal to at least 180 degrees plus a divergence angle of the emitted beams. In this regard, the above-described examples assume that each emitted beam diverges at a substantially similar angle about its depicted axis, but embodiments are not limited thereto.

Next, at S205, a three-dimensional image of the target is generated based on the first plurality of projection images and the second plurality of projection images. The three-dimensional image may be generated using any currently- or hereafter-known technique that is suitable in view of the locations at which the projection images were acquired. More particularly, the set of projection images represented in FIG. 5 as well as the set represented in FIG. 6 may lack some information required by conventional filter-back-projection reconstruction techniques. Accordingly, the three-dimensional image of the target may be generated at S205 using an iterative reconstruction technique (e.g., Algebraic Reconstruction Technique, Simultaneous Algebraic Reconstruction Technique) and/or other techniques that suitably account for unconventional scanning techniques and resulting gaps in projection data.

Figure 7:
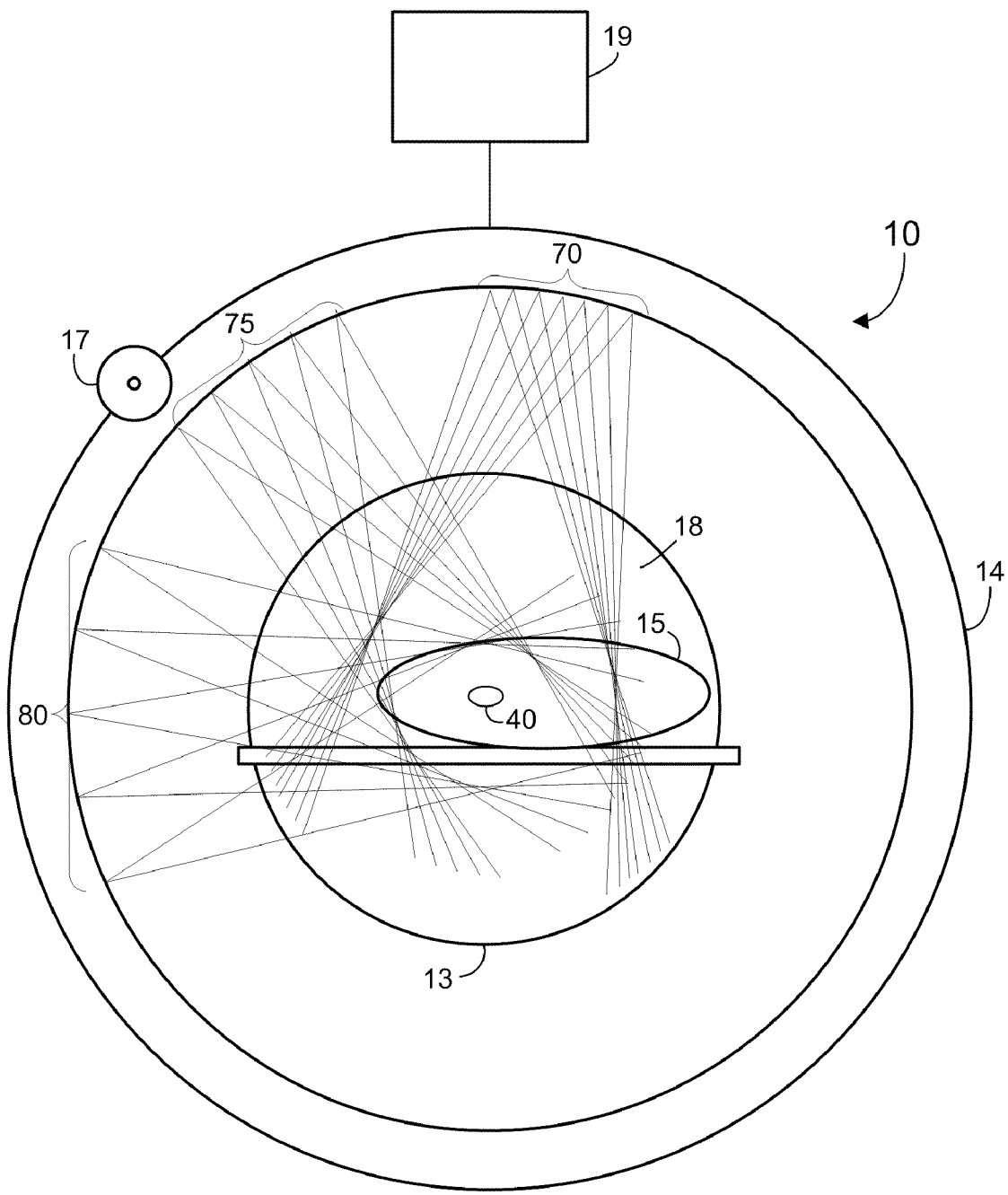
FIG. 7 is a diagram illustrating radiation emission locations and associated beam divergences according to some embodiments.

In some embodiments of process 200, at least one of the first plurality of radiation beams emitted at S201 exhibits a first divergence angle, and at least one of the second plurality of radiation beams emitted at S203 exhibits a second divergence angle different from the first divergence angle. An example of such an embodiment is illustrated in FIG. 7. In contrast to the beam axes illustrated in the previous figures, FIG. 7 depicts divergence angles of the illustrated fan beams.

Beams 70 each exhibit a first divergence angle and are emitted from locations spaced in a first density. The divergence angle may be controlled by collimating devices located in the device responsible for emitting the beam. Each of beams 75 exhibit a second divergence angle and are emitted from locations spaced in a second density which is greater than the first density. Finally, beams 80 also exhibit the second divergence angle but are emitted from locations spaced in a third density which is greater than the second density.

Projection images may be acquired based on beams 70, 75 and 80 as described with respect to process 200 and a three-dimensional image may be generated therefrom. As also described, the three-dimensional image may be generated based on projection images associated with radiation beams in addition to those illustrated in FIG. 7. In some embodiments, the locations, densities and divergence angles of the radiation beams may be selected to provide a suitable three-dimensional image of target 40 while reducing a dose received by other volumes of patient 15.

In addition to or alternatively of the foregoing, at least one of the first plurality of radiation beams emitted at S201 may associated with a first intensity, and the at least one of the second plurality of radiation beams emitted at S203 may be associated with a second dose rate different from the first intensity. In this regard, dose deposition is a known function of depth from a point at which radiation enters patient 15. The dose deposition function may therefore be taken into consideration when determining the respective intensities of the emitted beams.

Reducing the intensity of an emitted beam, for example, may increase noise into the generated three-dimensional image. Such an increase may be acceptable in view of the corresponding reduction in received dose.

Previously-acquired planning CT data may be used to create imaging protocols according to some embodiments. For example, a target volume and sensitive organs may be located within planning CT data. An imaging protocol according to some embodiments may then be created with the goal of generating suitable images of the target volume while reducing the dose received by the sensitive organs.

An imaging protocol may specify the distribution of locations from which imaging beams are to be emitted. The protocol may also associate each beam with a respective divergence angle and/or intensity. A planning system for generating such an imaging protocol may be constrained by requirements of the reconstruction technique to be used to generate the three-dimensional image. Such constraints may include, but are not limited to, a minimum density of the beam locations, a minimum exit fluence needed for image acquisition, and a minimum signal-to-noise ratio.

Figure 8:
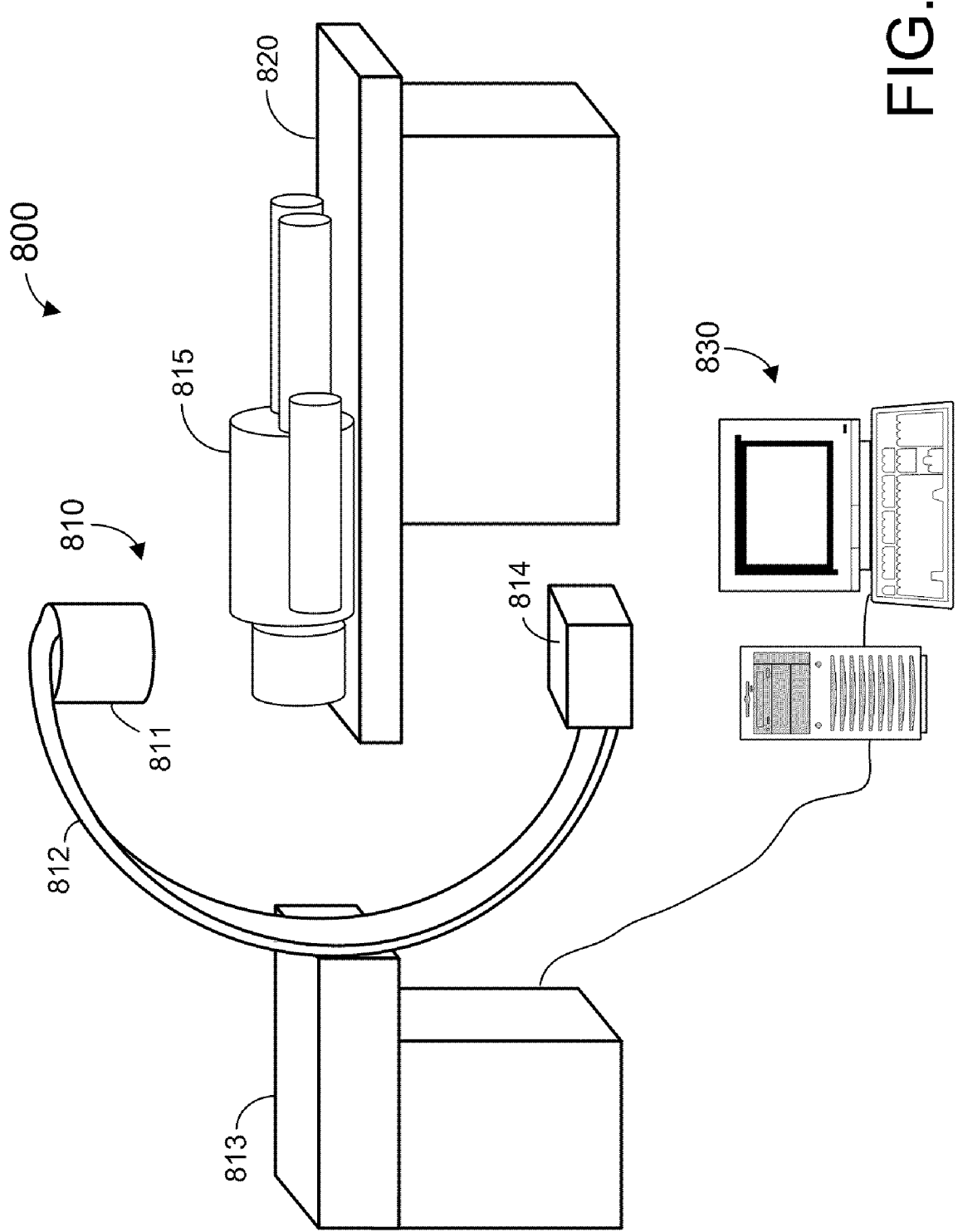
FIG. 8 is a diagram illustrating an image acquisition system according to some embodiments.

FIG. 8 illustrates system 800 to execute processes according to some embodiments described herein. System 800 includes kilovoltage imaging system 810, table 820 and operator station 830. Imaging system 810 comprises X-ray tube 811, C-arm 812, base 813 and imaging device 814. X-ray tube 811 may comprise any suitable device to emit imaging radiation, and, in some embodiments, emits kilovoltage radiation having energies ranging from 50 to 150 keV. Imaging device 814 may comprise a flat-panel imaging device or any other suitable type of imaging device.

X-ray tube 811 and imaging device 814 may be coupled to C-arm 812 so as to face one another irrespective of any movement of C-arm 812 with respect to base 813. In this regard, C-arm 812 is slidably mounted on base 813 and can therefore be moved in order to change the position of X-ray tube 811 with respect to body 815. Such movement may allow system 810 to acquire projection images from various emission locations around a target. These projection images may be used to generate three-dimensional images of the target as described above.

Unlike CT scanner 10, the radiation beams emitted by X-ray tube 811 may be cone-shaped. Cone-shaped radiation beams may be used in conjunction with any of the above-described embodiments. However, controlling the divergence angle of the cone-shaped beams may require different collimating devices than those mentioned above with respect to fan-shaped beams.

Many C-arm/base configurations may be used in conjunction with some embodiments, including configurations in which base 813 is rotatably mounted to a ceiling of a room containing system 800, configurations in which one C-arm is slidably mounted on another C-arm, and configurations incorporating multiple independent C-arms. Moreover, the foregoing processes may also be performed by a rotating linear accelerator emitting cone-shaped radiation beams having energies in the MeV range.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
   emitting a first plurality of x-ray radiation beams from respective ones of a first plurality of locations along a first arc;
   acquiring a first plurality of projection images of a target based on the first plurality of x-ray radiation beams;
   emitting a second plurality of x-ray radiation beams from respective ones of a second plurality of locations along a second arc;
   acquiring a second plurality of projection images of the target based on the second plurality of x-ray radiation beams; and
   generating a three-dimensional image of the target based on the first plurality of projection images and the second plurality of projection images,
   wherein a density of the first plurality of locations along the first arc is less than the density of the second plurality of locations along the second arc;
   wherein at least one of the first plurality of x-ray radiation beams exhibits a first divergence angle, and
   wherein at least one of the second plurality of x-ray radiation beams exhibits a second divergence angle different from the first divergence angle.

2. A method according to claim 1,
   wherein the at least one of the first plurality of x-ray radiation beams is associated with a first intensity, and
   wherein the at least one of the second plurality of x-ray radiation beams is associated with a second intensity different from the first intensity.

3. A method according to claim 1,
   wherein at least one of the first plurality of x-ray radiation beams exhibits a first divergence angle, and
   wherein at least one other of the first plurality of x-ray radiation beams exhibits a second divergence angle different from the first divergence angle.

4. A method according to claim 1,
   wherein at least one of the first plurality of x-ray radiation beams is associated with a first intensity, and
   wherein at least one of the second plurality of x-ray radiation beams is associated with a second intensity different from the first intensity.

5. A method according to claim 1, further comprising:
   emitting a third plurality of x-ray radiation beams from respective ones of a third plurality of locations along a third arc; and
   acquiring a third plurality of projection images of the target based on the third plurality of x-ray radiation beams,
   wherein generating the three-dimensional image of the target comprises:

generating the three-dimensional image based on the first plurality of projection images, the second plurality of projection images, and the third plurality of projection images, and wherein a density of the third plurality of locations along the third arc is different from the density of the first plurality of locations along the first arc and different from the density of the second plurality of locations along the second arc.

6. A system comprising:

an emission device to emit a first plurality of x-ray radiation beams from respective ones of a first plurality of locations along a first arc, and to emit a second plurality of x-ray radiation beams from respective ones of a second plurality of locations along a second arc;

an imaging device to acquire a first plurality of projection images of a target based on the first plurality of x-ray radiation beams, and to acquire a second plurality of projection images of the target based on the second plurality of x-ray radiation beams; and a processor to generate a three-dimensional image of the target based on the first plurality of projection images and the second plurality of projection images, wherein a density of the first plurality of locations along the first arc is less than the density of the second plurality of locations along the second arc; wherein at least one of the first plurality of x-ray radiation beams exhibits a first divergence angle, and wherein at least one of the second plurality of x-ray radiation beams exhibits a second divergence angle different from the first divergence angle.

7. A system according to claim 6, wherein the at least one of the first plurality of x-ray radiation beams is associated with a first intensity, and wherein the at least one of the second plurality of x-ray radiation beams is associated with a second intensity different from the first intensity.

8. A system according to claim 7, wherein at least one of the first plurality of x-ray radiation beams exhibits a first divergence angle, and wherein at least one other of the first plurality of x-ray radiation beams exhibits a second divergence angle different from the first divergence angle.

9. A system according to claim 6, wherein at least one of the first plurality of x-ray radiation beams is associated with a first intensity, and wherein at least one of the second plurality of x-ray radiation beams is associated with a second intensity different from the first intensity.

10. A system according to claim 6, wherein the emission device is to emit a third plurality of x-ray radiation beams from respective ones of a third plurality of locations along a third arc, wherein the imaging device is to acquire a third plurality of projection images of the target based on the third plurality of x-ray radiation beams, wherein generation of the three-dimensional image of the target comprises generation of the three-dimensional image based on the first plurality of projection images, the second plurality of projection images, and the third plurality of projection images, and wherein a density of the third plurality of locations along the third arc is different from the density of the first plurality of locations along the first arc and different from the density of the second plurality of locations along the second arc.

11. A method comprising:

acquiring a three-dimensional image including a target volume and one or more other volumes of a patient;

determining, based on the three-dimensional image, a distribution of locations from which respective x-ray imaging beams are to be emitted to generate projection images of the target volume from which a second three-dimensional image of the target volume can be generated, wherein the distribution of locations exhibits a non-uniform density; and determining, for each location, a divergence angle of a beam to be emitted therefrom, wherein a divergence angle of a beam to be emitted from a first one of the locations is different from a divergence angle of a beam to be emitted from a second one of the locations.

12. A method according to claim 11, further comprising:

determining, for each location, an intensity of a beam to be emitted therefrom, wherein an intensity of a beam to be emitted from a first one of the locations is different from an intensity of a beam to be emitted from a second one of the locations.

13. A method according to claim 12, wherein the determined intensities are based on a minimum exit fluence needed for image acquisition.

14. A method according to claim 11, wherein the determination is based on a minimum required density of the locations.

15. A method according to claim 11, wherein the determination is based on a desired quality of the second three-dimensional image of the target volume and minimization of a radiation dose received by the one or more other volumes.

* * * * *